United States Patent
Kitahashi et al.

(10) Patent No.: US 11,166,913 B2
(45) Date of Patent: *Nov. 9, 2021

(54) TUMOR THERAPEUTIC AGENT AND KIT CONTAINING GEMCITABINE LIPOSOME COMPOSITION

(71) Applicant: FUJIFILM Corporation, Tokyo (JP)

(72) Inventors: Tsukasa Kitahashi, Ashigarakami-gun (JP); Shinji Mima, Ashigarakami-gun (JP); Takeshi Matsumoto, Ashigarakami-gun (JP); Takahiro Sekiguchi, Ashigarakami-gun (JP); Mikinaga Mori, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 15/967,970

(22) Filed: May 1, 2018

(65) Prior Publication Data

US 2018/0243214 A1 Aug. 30, 2018

Related U.S. Application Data

(63) Continuation of application No. PCT/JP2016/082415, filed on Nov. 1, 2016.

(30) Foreign Application Priority Data

Nov. 2, 2015 (JP) .............................. JP2015-215768

(51) Int. Cl.
*A61K 9/127* (2006.01)
*A61K 47/24* (2006.01)
(Continued)

(52) U.S. Cl.
CPC ............ *A61K 9/127* (2013.01); *A61K 31/337* (2013.01); *A61K 31/7068* (2013.01);
(Continued)

(58) Field of Classification Search
CPC ........ A61K 9/127; A61K 47/24; A61K 47/28; A61K 31/337; A61K 31/7068; A61K 47/643; A61P 35/00; B82Y 5/00
See application file for complete search history.

(56) References Cited

U.S. PATENT DOCUMENTS 5,049,392 A * 9/1991 Weiner ................. A61K 9/1278
264/4.1
9,370,489 B2 * 6/2016 Yang .................... A61K 9/1272
(Continued)

FOREIGN PATENT DOCUMENTS

CN 101002733 A 7/2007
CN 102784107 A 11/2012
(Continued)

OTHER PUBLICATIONS

D.D. Von Hoff et al in Journal of Clinical Oncology, vol. 29, No. 34, Dec. 1, 2011, pp. 4548-4554.*
(Continued)

*Primary Examiner* — Gollamudi S Kishore
(74) *Attorney, Agent, or Firm* — Sughrue Mion, PLLC (57) ABSTRACT

An object of the present invention is to provide a tumor therapeutic agent and a kit which have superior antitumor effects as compared with gemcitabine, a taxane antitumor agent, and a combination therapy thereof which have been put on the market. According to the present invention, there is provided a tumor therapeutic agent obtained by combining a taxane antitumor agent with a liposome composition in which gemcitabine or a salt thereof is contained in a liposome.

4 Claims, 1 Drawing Sheet

(51) Int. Cl.
*A61K 47/28* (2006.01)
*A61K 31/337* (2006.01)
*A61K 31/7068* (2006.01)
*A61P 35/00* (2006.01)

(52) U.S. Cl.
CPC .............. *A61K 47/24* (2013.01); *A61K 47/28* (2013.01); *A61P 35/00* (2018.01)

(56) References Cited

U.S. PATENT DOCUMENTS

| | | | |
|---|---|---|---|
| 2005/0249795 A1* | 11/2005 | Zhang | A61K 9/1272 424/450 |
| 2007/0116753 A1 | 5/2007 | Hong et al. | |
| 2007/0178147 A1 | 8/2007 | Desai et al. | |
| 2010/0239652 A1* | 9/2010 | Rochlitz | A61K 9/127 424/450 |
| 2011/0002977 A1 | 1/2011 | Li et al. | |
| 2011/0064796 A1* | 3/2011 | Cipolla | A61P 31/00 424/450 |
| 2012/0171283 A1 | 7/2012 | Hong et al. | |
| 2013/0121912 A1* | 5/2013 | Yao | A61K 31/7088 424/1.11 |
| 2013/0122081 A1 | 5/2013 | Hong et al. | |
| 2013/0259922 A1 | 10/2013 | Haas et al. | |
| 2013/0302400 A1 | 11/2013 | Maneval et al. | |
| 2014/0154298 A1 | 6/2014 | Hong et al. | |
| 2015/0182460 A1 | 7/2015 | Hong et al. | |
| 2016/0008283 A1 | 1/2016 | Nel et al. | |
| 2016/0030341 A1 | 2/2016 | Hong et al. | |
| 2016/0030342 A1 | 2/2016 | Hong et al. | |
| 2016/0051500 A1 | 2/2016 | Wanebo et al. | |
| 2016/0081928 A1 | 3/2016 | Hong et al. | |
| 2016/0095817 A1 | 4/2016 | Hong et al. | |
| 2016/0095852 A1 | 4/2016 | Hong et al. | |
| 2016/0106672 A1 | 4/2016 | Hong et al. | |
| 2016/0338956 A1 | 11/2016 | Hong et al. | |
| 2016/0339014 A1 | 11/2016 | Hong et al. | |
| 2017/0042810 A1 | 2/2017 | Matsumoto et al. | |
| 2017/0042813 A1 | 2/2017 | Ono et al. | |
| 2017/0071858 A1 | 3/2017 | Hong et al. | |
| 2017/0079912 A1 | 3/2017 | Hong et al. | |
| 2017/0079913 A1 | 3/2017 | Hong et al. | |
| 2017/0079914 A1 | 3/2017 | Hong et al. | |
| 2017/0340624 A1 | 11/2017 | Hong et al. | |
| 2018/0169014 A1 | 6/2018 | Hong et al. | |
| 2018/0235954 A1 | 8/2018 | Hong et al. | |
| 2021/0275453 A1 | 9/2021 | Kitahashi et al. | |

FOREIGN PATENT DOCUMENTS

| | | |
|---|---|---|
| CN | 104411324 A | 3/2015 |
| EP | 2 656 835 A1 | 10/2013 |
| EP | 3 138 557 A1 | 3/2017 |
| JP | 2007-536247 A | 12/2007 |
| JP | 2013-526563 A | 6/2013 |
| JP | 2015-514109 A | 5/2015 |
| RU | 2494729 C2 | 10/2013 |
| WO | 2005/000266 A1 | 1/2005 |
| WO | 2005/021012 A1 | 3/2005 |
| WO | 2007/005754 A2 | 1/2007 |
| WO | 2011/144745 A2 | 11/2011 |
| WO | 2013087791 A1 | 6/2013 |
| WO | 092858 * | 6/2014 |
| WO | 2014/110555 A1 | 7/2014 |
| WO | 2015/166985 A1 | 11/2015 |
| WO | 2015/166987 A1 | 11/2015 |
| WO | 2017/192863 A1 | 11/2017 |

OTHER PUBLICATIONS

D. Cosco et al in Cancer Chemother Pharmacol., vol. 64, pp. 1009-1020, 2009.*
M. Celano et al in BMC Cancer, vol. 4, pp. 1-5, 2004.*
C. Federico et al in International Journal of Nanomedicine, vol. 7, pp. 5423-5436, 2012.*
Anne-Laure Papa et al., "PEGylated liposomal Gemcitabine: insights into a potential breast cancer therapeutic", Cellular Oncology, vo. 36, No. 6, pp. 449-457, XP055511227, Oct. 1, 2013 (9 pages total).
Qinmei Zhou et al., "Analysis of gemcitabine liposome injection by HPLC with evaporative light scattering detection", Journal of Liposome Research, vo. 22, No. 4, Jan. 1, 2002, pp. 263-269, XP009508406 (7 pages total).
Extended European Search Report dated Oct. 15, 2018, issued by the European Patent Office in counterpart European application No. 16862068.0.
Cosco, Donato et al., "Liposomes as multicompartmental carriers for multidrug delivery in anticancer chemotherapy", Drug Delivery and Translational Research, 2011, pp. 66-75, vol. 1 (10 pages total).
Liboiron, Barry D. et al., "Nanoscale delivery systems for combination chemotherapy", Drug Delivery in Oncology, 2012, pp. 1013-1050, vol. 2 (38 pages total).
Von Hoff, Daniel D. et al., "Increased Survival in Pancreatic Cancer with nab-Paclitaxel plus Gemcitabine", N Engl J Med., 2013, pp. 1691-1703, vol. 369, No. 18 (18 pages total).
Hideki UENO et al., "Systemic chemotherapy for advanced pancreatic cancer", Journal of Clinical and Experimental Medicine, Feb. 21, 2015, pp. 887-892, vol. 252, No. 8 (6 pages total).
Daniel D. Von Hoff et al., "Increased Survival in Pancreatic Cancer with nab-Paclitaxel plus Gemcitabine", The New England Journal of Medicine, 2013, pp. 1691-1703, vol. 369, No. 18 (13 pages total).
William J. Gradishar et al., "Phase III Trial of Nanoparticle Albumin-Bound Paclitaxel Compared With Polyethylated Castor Oil-Based Paclitaxel in Women With Breast Cancer", Journal of Clinical Oncology, Nov. 1, 2005, pp. 7794-7803, vol. 23, No. 31 (10 pages total).
Kathy S. Albain et al., "Gemcitabine Plus Paclitaxel Versus Paclitaxel Monotherapy in Patients With Metastatic Breast Cancer and Prior Anthracycline Treatment", Journal of Clinical Oncology, Aug. 20, 2008, pp. 3950-3957, vol. 26, No. 24 (8 pages total).
P.K. Working et al., "Pharmacokinetics, Biodistribution and Therapeutic Efficacy of Doxorubicin Encapsulated in Stealth® Liposomes (DOXIL®)", Journal of Liposome Research, 1994, pp. 667-687, vol. 4. No. 1 (21 pages total).
Kazuo Maruyama, "Passive targeting with liposomal drug carriers", Drug Delivery System, 1999, pp. 433-447, vol. 14, No. 6 (15 pages total).
International Search Report of PCT/JP2016/082415 dated Dec. 27, 2016 [PCT/ISA/210].
Written Opinion of PCT/JP2016/082415 dated Dec. 27, 2016 [PCT/ISA/237].
International Preliminary Report on Patentability dated May 8, 2018 issued by the International Bureau in PCT/JP2016/082415.
Notification of Reasons for Refusal dated Feb. 12, 2019 from the Japanese Patent Office in counterpart Japanese Application No. 2017-548769.
Office Action dated May 21, 2019, from the Russian Federal Service for Intellectual Property in counterpart Russian Application No. 2018119680/04.
Office Action dated Jun. 18, 2019, from the Japanese Patent Office in counterpart Japanese Application No. 2017-548769.
"Efficiency of a combination of nab-paclitaxel with gemcitabine in the metastatic pancreatic cancer", Oncology News, http://rosoncoweb.ru/news/oncology/2013/02/05/, Feb. 5, 2013, (2 pages total).
Office Action dated Nov. 13, 2019 from the State Intellectual Property Office of the P.R.C. in Chinese application No. 201680064060.7.
Jing, Yao, "Application Directory of Pharmaceutical Excipients", China Medical Science Press, Aug. 31, 2011, p. 264 (2 pages).
Office Action dated Sep. 26, 2019, from the Russian Federal Service for Intellectual Property in counterpart Russian Application No. 2018119680/04.
Office Action dated Sep. 3, 2019, from the Korean Intellectual Property Office in Korean Application No. 10-2018-7012568.
Summons to the Oral Proceeding dated Mar. 2, 2020 from European Patent Office in corresponding EP Application No. 16 862 068.0.
Office Action dated Jun. 12, 2020 in U.S. Appl. No. 16/808,004.

(56) References Cited

OTHER PUBLICATIONS

Trosko et al., "Mechanism of up-regulated gap junctional intercellular communication during chemoprevention and chemotherapy of cancer", Mutation Research, 2001, vol. 480-481, pp. 219-229 (11 pages total).
Office Action dated Jun. 24, 2020 in Chinese Application No. 201680064060.7.
Frese et al., "nab-Paclitaxel Potentiates Gemcitabine Activity by Reducing Cytidine Deaminase Levels in a Mouse Model of Pancreatic Cancer", Cancer Discovery, Mar. 2012, vol. 2, pp. 260-269 (11 pages total).
N. A. Oborotova et al., "Thermosensitive Liposome Drug Forms in the Experimental Oncology", Russian Biotherapeutic Journal, vol. 5, No. 1, 2006, pp. Oncology, Rossiiskii terapevticheskii zhurnal (Russian Biotherapeutic Journal), vol. 5, No. 1, 2006, pp. 62-70, 9 pages total.
Office Action dated Feb. 25, 2020 in Russian Application No. 2018119680/04.
Office Action dated Oct. 8, 2020 by the U.S. Patent Office in U.S. Appl. No. 16/808,004.
Translation of Office Action dated Mar. 31, 2021 issued by the Russian Patent Office in Russian Application No. 2020137384/04.
N.B. Demina et al., Development Strategy and Biopharmaceutical Aspects of Drug Delivery Systems // Russian Chemistry Journal, 2012, vol. 56, N. 3-4, pp. 5-10, p. 8 (6 pages).
Pharmaceutical Technology: Pharmaceutics, Textbook for University Students, I.I. Krosniuk, G.V. Mikhaylova, 2nd edition, stereotyped, Moscow, Academia Publishing Center, 2006, pp. 297-299 (4 pages).
Office Action dated Mar. 2, 2021, from the Intellectual Property Office of India in Indian Application No. 202048043278.
Office Action dated Mar. 31, 2021 issued by the Russian Patent Office in Russian Application No. 2020137384/04.
Office Action dated Mar. 31, 2021 issued by the Russian Patent Office in Russian Application No. 2020137385/04.
Office Action dated Feb. 9, 2021, from the Indian Patent Office in Indian Application No. 202048043283.
Advisory Action dated Jan. 21, 2021 in U.S. Appl. No. 16/808,004.
Office Action dated Jul. 26, 2019, from the European Patent Office in counterpart European Application No. 16 862 068.0
Office Action dated Jul. 26, 2019, from the Indian Patent Office in counterpart Indian Application No. 201847016588.
Notice of Allowance dated Jul. 8, 2021 in U.S. Appl. No. 16/808,004.
Office Action dated Sep. 3, 2021 in Chinese Application No. 202010466486.3.
Office Action dated Aug. 26, 2021 in Russian Application No. 2020137385.
Soema et al., "Predicting the influence of liposomal lipid composition on liposome size, zeta potential and liposome-induced dendritic cell maturation using a design of experiments approach", European Journal of Pharmaceutics and Biopharmaceutics, 2015, vol. 94, pp. 427-435 (9 pages total).

* cited by examiner

TUMOR THERAPEUTIC AGENT AND KIT CONTAINING GEMCITABINE LIPOSOME COMPOSITION

CROSS-REFERENCE TO RELATED APPLICATIONS

This application is a Continuation of PCT International Application No. PCT/JP2016/082415 filed on Nov. 1, 2016, which claims priority under 35 U.S.C § 119(a) to Japanese Patent Application No. 2015-215768 filed on Nov. 2, 2015. Each of the above application(s) is hereby expressly incorporated by reference, in its entirety, into the present application.

BACKGROUND OF THE INVENTION

1. Field of the Invention

The present invention relates to a tumor therapeutic agent obtained by combining a taxane antitumor agent with a liposome composition in which gemcitabine or a salt thereof is contained in a liposome, and a kit for treating a tumor which contains a taxane antitumor agent and a liposome composition in which gemcitabine or a salt thereof is contained in a liposome.

2. Description of the Related Art

Gemcitabine is used as a useful drug in chemotherapy of malignant tumors. However, an efficiency of gemcitabine single agent to a tumor is as low as 10%, and the survival period of cancer patients is known to be short (a median survival period of 6.7 months) (The New England Journal of Medicine, 2013, 369 (18), 1691-1703).

In the chemotherapy of malignant tumors, taxane antitumor agents such as paclitaxel or nab-paclitaxel are also used as useful drugs. However, the efficiency of a taxane antitumor single agent to a tumor is as low as 10 to 25%, and the survival period of cancer patients is known to be short (a survival period of 12 to 15 months) (Journal of Clinical Oncology, 2005, 23 (31), 7794-7803).

In clinical practice, multi-drug combination therapy is being performed in order to compensate for the difference in susceptibility of each antitumor agent to tumor and to enhance the drug efficacy. For example, a combination of gemcitabine and abraxane, a combination of gemcitabine and paclitaxel, and a combination of gemcitabine and nab-paclitaxel are known. However, the efficiency of a combination of gemcitabine and paclitaxel to patients with breast cancer is 41.4% and a median survival period is 18.6 months (Journal of Clinical Oncology, 2008, 26 (24), 3950-3957). In addition, the efficiency of a combination of gemcitabine and nab-paclitaxel to patients with pancreatic cancer is 23% and a median survival period is 8.5 months (The New England Journal of Medicine, 2013, 369 (18), 1691-1703).

A liposome is a closed endoplasmic reticulum formed of a lipid bilayer membrane using a lipid, and its application as a carrier for a drug delivery system has been studied. It is known that, by containing a drug in a liposome, stability in blood and in vivo distribution of a drug can be changed and reachability to target tissues can be improved (Journal of Liposome Research, 1994, 4, 667-687). In addition, it is known that liposomes with a particle diameter of 100 to 200 nm easily accumulate in cancer tissues (Drug Delivery System, 1999, 14, 433-447).

SUMMARY OF THE INVENTION

One of the causes of the low antitumor effect with gemcitabine single agent is, for example, a short retention time of gemcitabine in blood. Gemcitabine shows a strong drug efficacy in a time-dependent manner. However, its retention time in blood is as short as 20 minutes, and therefore, it has not been able to exhibit a sufficient antitumor effect. In addition, another cause of the low antitumor effect with gemcitabine single agent is, for example, low selectivity of gemcitabine to tumor tissues. In a case where an antitumor agent is administered, it may be eliminated quickly from blood or may be distributed to organs other than the target. Therefore, the antitumor agent does not always effectively accumulate in tumor tissues. For this reason, many antitumor agents cannot sufficiently exhibit an antitumor action on tumor tissues and are often accompanied by an undesirable action on normal tissues (side effects), causing severe toxicity.

One of the causes of the low antitumor effect of a taxane antitumor single agent is that, for example, the taxane sensitivity for each tumor greatly differs and the efficiency for a patient to be treated does not rise. For this reason, it is necessary to use an antitumor agent with a different mechanism in addition to the taxane antitumor agent in combination.

In addition, it cannot be said that even the combination therapy disclosed in Journal of Clinical Oncology, 2008, 26 (24), 3950-3957 and in The New England Journal of Medicine, 2013, 369 (18), 1691-1703 has sufficiently high therapeutic effects.

An object of the present invention is to provide a tumor therapeutic agent and a kit for treating a tumor which have superior antitumor effects as compared with gemcitabine, taxane antitumor agent, and a combination therapy thereof which have been put on the market.

The present inventors have conducted intensive studies. As a result, they have found that the antitumor effect is enhanced by combining a taxane antitumor agent with a liposome composition in which gemcitabine or a salt thereof is contained in a liposome, and have completed the present invention.

That is, the present invention provides the following.

(1) A tumor therapeutic agent obtained by combining a taxane antitumor agent with a liposome composition in which gemcitabine or a salt thereof is contained in a liposome.
(2) The tumor therapeutic agent according to (1), in which the taxane antitumor agent is paclitaxel or a salt thereof, or nab-paclitaxel.
(3) The tumor therapeutic agent according to (1) or (2), in which the taxane antitumor agent is nab-paclitaxel.
(4) The tumor therapeutic agent according to any one of (1) to (3), in which a content ratio of cholesterols to a total amount of a lipid forming the liposome is 10 mol % to 35 mol %, and an osmotic pressure of an inner aqueous phase of the liposome is 2 to 8 times an osmotic pressure of an outer aqueous phase of the liposome.
(5) The tumor therapeutic agent according to any one of (1) to (4), in which the liposome is a single lamella.
(6) The tumor therapeutic agent according to any one of (1) to (5), in which a release rate of gemcitabine or a salt thereof from the liposome composition in plasma is 10 mass %/24 hr to 70 mass %/24 hr.
(7) The tumor therapeutic agent according to any one of (1) to (6), in which the lipid forming the liposome contains hydrogenated soybean phosphatidylcholine, 1,2-distearoyl-3-phosphatidylethanolamine-polyethylene glycol, and cholesterol.

(8) The tumor therapeutic agent according to any one of (1) to (7), in which an average particle diameter of the liposome is 2 nm to 200 nm.

(9) A kit for treating a tumor, comprising: a liposome composition in which gemcitabine or a salt thereof is contained in a liposome; and a taxane antitumor agent.

In addition, the present invention provides the following.

(10) An antitumor effect enhancing agent which is administered in combination with one or more antitumor agents selected from taxane antitumor agents, comprising: a liposome composition in which gemcitabine or a salt thereof is contained in a liposome.

(11) The antitumor effect enhancing agent according to (10), in which the taxane antitumor agent is paclitaxel or a salt thereof, or nab-paclitaxel.

(12) The antitumor effect enhancing agent according to (10) or (11), in which the taxane antitumor agent is nab-paclitaxel.

(13) The antitumor effect enhancing agent according to any one of (10) to (12), in which a content ratio of cholesterols to a total amount of a lipid forming a liposome is 10 mol % to 35 mol %, and an osmotic pressure of an inner aqueous phase of the liposome is 2 to 8 times an osmotic pressure of an outer aqueous phase of the liposome.

(14) The antitumor effect enhancing agent according to any one of (10) to (13), in which the liposome is a single lamella.

(15) The antitumor effect enhancing agent according to any one of (10) to (14), in which a release rate of gemcitabine or a salt thereof from the liposome composition in plasma is 10 mass %/24 hr to 70 mass %/24 hr.

(16) The antitumor effect enhancing agent according to any one of (10) to (15), in which the lipid forming the liposome contains hydrogenated soybean phosphatidylcholine, 1,2-distearoyl-3-phosphatidylethanolamine-polyethylene glycol, and cholesterol.

(17) The antitumor effect enhancing agent according to any one of (10) to (16), in which an average particle diameter of the liposome is 2 nm to 200 nm.

Furthermore, the present invention provides the following.

(18) A method for treating a tumor comprising: combining a therapeutically effective dose in a case where a liposome composition in which gemcitabine or a salt thereof is contained in a liposome is used for combination therapy, with a therapeutically effective dose in a case where a taxane antitumor agent is used for combination therapy; and administering the combination to a target.

(19) A method for treating a tumor comprising: administering a therapeutically effective dose in a case where a liposome composition in which gemcitabine or a salt thereof is contained in a liposome is used for combination therapy and a therapeutically effective dose in a case where a taxane antitumor agent is used for combination therapy to a target simultaneously, separately, continuously, or at intervals.

Furthermore, the present invention provides the following.

(20) A use of a liposome composition in which gemcitabine or a salt thereof is contained in a liposome for producing a tumor therapeutic agent obtained by combining the liposome composition in which the gemcitabine or the salt thereof is contained in the liposome with one or more antitumor agents selected from taxane antitumor agents.

(21) A liposome composition in which gemcitabine or a salt thereof is contained in a liposome for treating a tumor, in which the liposome composition is used so as to be administered in combination with one or more antitumor agents selected from taxane antitumor agents.

The tumor therapeutic agent and the kit for treating a tumor of the present invention have superior tumor regression and tumor growth delaying effects as compared with a gemcitabine single agent, a taxane antitumor single agent, or a combined use of the gemcitabine and the taxane antitumor agent.

DESCRIPTION OF THE PREFERRED EMBODIMENTS

In the present specification, the numerical range represented by "to" indicates a range including numerical values denoted before and after "to" as a minimum value and a maximum value.

In the present invention, unless otherwise specified, % means a mass percentage.

In the present specification, the amount of each component in a composition means, unless otherwise specified, a total amount of a plurality of substances present in the composition in a case where the plurality of substances corresponding to each component are present in the composition.

The "release" means that a drug contained in a liposome passes through a lipid membrane forming the liposome and is released to the outside of the liposome.

The "release rate" means an amount of a drug contained in a liposome which passes through the lipid membrane forming the liposome and is released to the outside of the liposome, per unit time.

"Retentivity in blood" means a property in which a drug in a state of being contained in a liposome is present in blood in a target to which a liposome composition is administered.

The "average particle diameter of the liposome" means a volume average particle diameter of liposomes present in a liposome composition. The average particle diameter of liposomes contained in the liposome composition of the present invention is measured through a dynamic light scattering method. Examples of commercially available determination devices using dynamic light scattering include a concentrated particle analyzer FPAR-1000 (manufactured by OTSUKA ELECTRONICS Co., LTD.), NANO-TRAC UPA (manufactured by Nikkiso Co., Ltd.), and NANOSIZER (manufactured by Malvern Instruments Ltd.)

The "target" is a mammal, such as a human, a mouse, a monkey, or a domestic animal, requiring prevention or treatment of a tumor, and is preferably a human who requires prevention or treatment thereof.

Examples of the "tumor" include breast cancer, endometrial cancer, ovarian cancer, prostate cancer, lung cancer, stomach cancer (gastric adenocarcinoma), non-small-cell lung cancer, pancreatic cancer, head and neck squamous cell cancer, esophageal cancer, bladder cancer, melanoma, colorectal cancer, renal cell carcinoma, non-Hodgkin lymphoma, and urothelial cancer.

Hereinafter, the present invention will be described in detail.

(Taxane Antitumor Agent)

Examples of the taxane antitumor agent include a pharmaceutical composition, which contains a taxane ring or a compound having a structure analogous to the taxane ring, as an active component.

Specific examples of the taxane antitumor agent include paclitaxel, docetaxel, cabazitaxel, tesetaxel, and ortataxel, and salts or derivatives thereof.

Examples of the salt include salts of basic groups such as amino groups, and acidic groups such as hydroxyl groups and carboxyl groups, which are commonly known.

Examples of the salts of basic groups include salts of mineral acids such as hydrochloric acid, hydrobromic acid, nitric acid, and sulfuric acid; salts of organic carboxylic acids such as formic acid, acetic acid, citric acid, oxalic acid, fumaric acid, maleic acid, succinic acid, malic acid, tartaric acid, aspartic acid, and trichloroacetic acid and trifluoroacetic acid; and salts of sulfonic acids such as methanesulfonic acid, benzenesulfonic acid, p-toluenesulfonic acid, mesitylenesulfonic acid, and naphthalenesulfonic acid.

Examples of salts of acidic groups include salts of alkali metals such as sodium and potassium; salts of alkaline earth metals such as calcium and magnesium; ammonium salts; and salts of nitrogen-containing organic bases such as trimethylamine, triethylamine, tributylamine, pyridine, N,N-dimethylaniline, N-methylpiperidine, N-methylmorpholine, diethylamine, dicyclohexylamine, procaine, dibenzylamine, N-benzyl-β-phenethylamine, 1-ephenamine, and N,N'-dibenzylethylenediamine.

An example of derivatives of paclitaxel includes nab-paclitaxel (albumin-bound paclitaxel).

As a taxane antitumor agent, paclitaxel or a salt thereof or nab-paclitaxel is preferable, and nab-paclitaxel is more preferable.

The taxane antitumor agent may contain additives such as an excipient, a binder, a lubricant, a disintegrator, a coloring agent, a flavoring agent, an emulsifying agent, a surfactant, a solubilizing agent, a suspending agent, an isotonic agent, a buffer agent, a preservative, an antioxidant, a stabilizer, and an absorption promoter which have been used for formulation.

Examples of administration routes of the taxane antitumor agent include an intravenous injection method, an intraarterial injection method, an intrarectal injection method, an intraperitoneal injection method, an intramuscular injection method, an intratumoral injection method, or an intravesical injection method, or methods such as oral administration, transdermal administration, and a method using suppositories. Regarding the dosage and the number of times of administration for adults, 0.01 to 1,000 mg/kg of a drug can be administered, for example, once or several times dividedly per day through oral or non-oral administration (for example, injection, instillation, and administration to a colorectal site). Examples of dosage forms include tablets, capsules, powders, syrups, granules, pills, suspensions, emulsions, solutions, powder formulations, suppositories, eye drops, nasal drops, ear drops, patches, ointments, and injections.

(Liposome)

A liposome is a closed endoplasmic reticulum formed of a lipid bilayer membrane using a lipid and has an aqueous phase (inner aqueous phase) in a space of the closed endoplasmic reticulum. The inner aqueous phase contains water and the like. Liposomes usually exist in a state of being dispersed in an aqueous solution (outer aqueous phase) on the outside of the closed endoplasmic reticulum. A liposome may be a single lamella (also called a monolayer lamella or a unilamella, with a single layer structure of a bilayer membrane), or may be a multilayer lamella (also called a multilamella with a structure of multiple bilayer membranes having an onion shape in which each of the layers is partitioned by a watery layer). However, a liposome of a single lamella is preferable in the present invention from the viewpoints of safety and stability in medical use.

The form of the liposome is not particularly limited as long as it is a liposome capable of containing a drug. The "containing" means a form in which a drug is included in an inner aqueous phase and the membrane itself of the liposome. For example, a form in which a drug is contained in a closed space formed of a membrane, a form in which a drug is contained in a membrane itself, or a combination thereof may be used.

The average particle diameter of liposomes is not particularly limited, but is preferably 2 nm to 200 nm, more preferably 5 nm to 150 nm, still more preferably 5 nm to 120 nm, and most preferably 5 nm to 100 nm.

It is preferable that a liposome has a spherical shape or a shape close thereto.

Components forming a lipid bilayer of a liposome are selected from lipids. A lipid dissolving in a mixed solvent of a water-soluble organic solvent and an ester-based organic solvent can be optionally used as the lipids. Examples of the lipids include phospholipids, lipids other than phospholipids, cholesterols, and derivatives thereof. These components may be formed of a single component or plural kinds of components.

Examples of phospholipids include natural or synthetic phospholipids such as phosphatidylcholine (lecithin), phosphatidylglycerol, phosphatidic acid, phosphatidylethanolamine, phosphatidylserine, phosphatidylinositol, sphingomyelin, and cardiolipin, or a substance hydrogenated thereto (for example, hydrogenated soybean phosphatidylcholine (HSPC)). Among these, hydrogenated phospholipids such as hydrogenated soybean phosphatidylcholine or sphingomyelin are preferable, and hydrogenated soybean phosphatidylcholine is more preferable. In the present invention, "phospholipids" also include phospholipid derivatives modified with phospholipids.

An example of lipids other than phospholipids includes lipids not containing phosphoric acid. Examples thereof include glycerolipids having no phosphoric acid moiety in its molecule and sphingolipids having no phosphoric acid moiety in its molecule. In the present invention, "lipids other than phospholipids" also include derivatives of lipids other than phospholipids modified with lipids other than phospholipids.

In a case of a substance in which a compound having a basic functional group is bonded to a lipid, the lipid is called a cationized lipid. The cationized lipid can modify, for example, a membrane of a liposome, and therefore, it is possible to enhance the adhesiveness and the like to cells as target sites.

Examples of cholesterols include cholesterol, in which cyclopentahydrophenanthrene is a basic skeleton and a part or all of the carbon is hydrogenated, and a derivative thereof. An example thereof includes cholesterol. In a case where the average particle diameter is reduced to less than or equal to 100 nm, the curvature of a lipid membrane increases. Since distortion of membranes arranged in liposomes also increases, a water-soluble drug is more likely to leak out. It is effective to add cholesterol or the like in order to fill the distortion of membranes due to lipids (membrane stabilizing effect) as means to suppress the leakage.

It is expected that the addition of cholesterols to liposomes lowers the fluidity of membranes of the liposomes by, for example, filling the gap between the membranes of the liposomes. In general, it is desirable that cholesterols are usually contained in liposomes in an amount of about 50 mol % in the total (total lipid) mol of lipid components. However, in liposomes with a high osmotic pressure of an inner aqueous phase, the optimal range of the amount of cholesterols has not been known.

The content ratio of cholesterols with respect to the total amount of lipids forming the liposome according to the present invention is 10 mol % to 35 mol %, preferably 15 mol % to 25 mol %, and more preferably 17 mol % to 21 mol %. By setting the content ratio of cholesterols with respect to the total amount of lipids forming the liposome to 10 mol % to 35 mol %, it is possible to obtain a liposome composition in which both ease of drug release and storage stability are achieved.

In addition to the above-described components, a hydrophilic polymer or the like for improving retentivity in blood, a fatty acid, diacetyl phosphate, or the like as a stabilizer of a membrane structure, and α-tocopherol or the like as an antioxidant may be added to a liposome. In the present invention, it is preferable not to use additives such as surfactants, for example, dispersion assistants which are not permitted for use in intravenous injection in medicinal use.

In the liposome according to the present invention, phospholipids, lipids other than phospholipids, cholesterols, or cholesterols are preferably modified with hydrophilic polymers, as phospholipids, lipids other than phospholipids, cholesterols, and derivatives thereof.

Examples of hydrophilic polymers include polyethylene glycols, polyglycerins, polypropylene glycols, polyvinyl alcohol, styrene-maleic acid anhydride alternating copolymers, polyvinyl pyrrolidone, and synthetic polyamino acid. The above-described hydrophilic polymers can be used alone or in combination of two or more thereof.

Among these, from the viewpoint of retentivity in blood of a formulation, polyethylene glycols, polyglycerins, and polypropylene glycols are preferable, and polyethylene glycol (PEG), polyglycerin (PG), and polypropylene glycol (PPG) are more preferable. Polyethylene glycol (PEG) is more preferable from the viewpoints of versatility and retentivity in blood.

The molecular weight of PEG is not particularly limited, but is 500 Dalton to 10,000 Dalton, preferably 1,000 Dalton to 7,000 Dalton, and more preferably 2,000 Dalton to 5,000 Dalton.

In the liposome according to the present invention, it is preferable to use a lipid modified with PEG (PEG-modified lipid) together with a main lipid contained in the liposome. Examples of PEG-modified lipids include 1,2-distearoyl-3-phosphatidylethanolamine-PEG2000 (manufactured by NOF CORPORATION), 1,2-distearoyl-3-phosphatidylethanolamine-PEG5000 (manufactured by NOF CORPORATION), and 1,2-distearoyl-3-phosphatidylethanolamine-polyethylene glycol such as distearoyl glycerol-PEG2000 (manufactured by NOF CORPORATION). These PEG-modified lipids may be added such that 0.3 to 50 mass %, preferably 0.5 to 30 mass %, and more preferably 1 to 20 mass % is contained with respect to the total lipid amount.

In the liposome according to the present invention, a combination of hydrogenated soybean phosphatidylcholine (a lipid contained in the liposome), 1,2-distearoyl-3-phosphatidylethanolamine-polyethylene glycol (a lipid used together with a main lipid), and a lipid of cholesterol is preferable.

In the liposome according to the present invention, it is preferable not to contain an anionic polymer (polyanion).

(Drug)

The liposome according to the present invention contains at least gemcitabine or a salt thereof as a drug.

Examples of the salt of gemcitabine include salts of basic groups such as amino groups, and acidic groups such as hydroxyl groups and carboxyl groups, which are commonly known.

Examples of the salts of basic groups include salts of mineral acids such as hydrochloric acid, hydrobromic acid, nitric acid, and sulfuric acid; salts of organic carboxylic acids such as formic acid, acetic acid, citric acid, oxalic acid, fumaric acid, maleic acid, succinic acid, malic acid, tartaric acid, aspartic acid, and trichloroacetic acid and trifluoroacetic acid; and salts of sulfonic acids such as methanesulfonic acid, benzenesulfonic acid, p-toluenesulfonic acid, mesitylenesulfonic acid, and naphthalenesulfonic acid.

Examples of salts of acidic groups include salts of alkali metals such as sodium and potassium; salts of alkaline earth metals such as calcium and magnesium; ammonium salts; and salts of nitrogen-containing organic bases such as trimethylamine, triethylamine, tributylamine, pyridine, N,N-dimethylaniline, N-methylpiperidine, N-methylmorpholine, diethylamine, dicyclohexylamine, procaine, dibenzylamine, N-benzyl-β-phenethylamine, 1-ephenamine, and N,N'-dibenzylethylenediamine.

Hydrochloride is preferable as the salt of gemcitabine.

The content of gemcitabine is preferably 0.1 to 2.0 mg/ml and more preferably 0.2 to 1.0 mg/ml with respect to the liposome composition.

(Drug Contained in Dissolved State)

The drug (gemcitabine or a salt thereof) contained in the liposome according to the present invention is present in a dissolved state in an inner aqueous phase of the liposome. Here, the dissolved state is regarded as a condition in which a drug is contained in a dissolved state in a case where the amount of the drug loaded with respect to the volume of the liposome is less than or equal to saturated solubility of the drug in the composition liquid of the inner aqueous phase. In addition, in a case where drug crystal is not observed with Cryo-TEM even at greater than or equal to saturated solubility, or in a case where no diffraction pattern due to crystal lattice is observed through XRD measurement, it is regarded that most of the drug contained in the liposome dissolves and is contained in a dissolved state. In this case, it is estimated that dissolution enhancement due to physicochemical environment created by the lipid membrane or partial incorporation of a drug into the lipid membrane occurs.

(Liposome Composition)

The liposome composition according to the present invention can contain a liposome containing gemcitabine or a salt thereof and an aqueous solution in which liposomes are dispersed.

In the liposome according to the present invention, the osmotic pressure of the inner aqueous phase of the liposome is preferably 2 to 8 times, more preferably 2.5 to 6 times, and still more preferably 3 to 5 times the outer aqueous phase of the liposome. By setting the osmotic pressure of the inner aqueous phase to 2 to 8 times the osmotic pressure of the outer aqueous phase, it is possible to achieve both ease of drug release and storage stability.

It is possible to appropriately add an aqueous solvent, an additive, and the like to the liposome composition. The liposome composition may contain at least one of a pharmaceutically acceptable isotonic agent, a stabilizer, an antioxidant, and a pH adjuster in relation to the administration route.

The isotonic agents are not particularly limited, but examples thereof include inorganic salts such as sodium chloride, potassium chloride, sodium hydrogen phosphate, sodium dihydrogen phosphate, and potassium dihydrogen phosphate, polyols such as glycerol, mannitol, and sorbitol, and saccharides such as glucose, fructose, lactose, or sucrose.

The stabilizer is not particularly limited, but examples thereof include saccharides such as glycerol, mannitol, sorbitol, lactose, or sucrose.

The antioxidants are not particularly limited, but examples thereof include ascorbic acid, uric acid, tocopherol homologues (for example, vitamin E or four isomers of tocopherol α, β, γ, and δ) cysteine, and ethylenediaminetetraacetic acid (EDTA). The above-described stabilizer and antioxidant can be used alone or in combination of two or more thereof.

Examples of pH adjusters include sodium hydroxide, citric acid, acetic acid, triethanolamine, sodium hydrogen phosphate, sodium dihydrogen phosphate, and potassium hydrogen phosphate.

The liposome composition may contain a pharmaceutically acceptable organic solvent, collagen, polyvinyl alcohol, polyvinyl pyrrolidone, carboxyvinyl polymer, sodium carboxymethyl cellulose, sodium polyacrylate, sodium alginate, water soluble dextran, sodium carboxymethyl starch, pectin, methyl cellulose, ethyl cellulose, xanthan gum, gum arabic, casein, gelatin, agar, diglycerin, propylene glycol, polyethylene glycol, vaseline, paraffin, stearyl alcohol, stearic acid, human serum albumin (HSA), mannitol, sorbitol, lactose, PBS, sodium chloride, saccharides, an in vivo degradable polymer, a serum-free medium, and an additive which is acceptable as a pharmaceutical additive.

In particular, the liposome composition according to the present invention preferably contains ammonium sulfate, L-histidine, purified white sugar, sodium hydroxide, or hydrochloric acid.

A container to be filled with the liposome composition is not particularly limited, but it is preferably a material having low oxygen permeability. An example thereof includes a bag using a laminate film having a plastic container, a glass container, an aluminum foil, an aluminum vapor deposition film, an aluminum oxide vapor deposition film, a silicon oxide vapor deposition film, polyvinyl alcohol, an ethylene vinyl alcohol copolymer, polyethylene terephthalate, polyethylene naphthalate, polyvinylidene chloride, and the like as a gas barrier layer. It is possible to shield light by employing a bag as necessary in which colored glass, aluminum foil, aluminum vapor deposition film, or the like is used.

In the container filled with the liposome composition, it is preferable to replace gas in a container space portion and in a drug solution with an inert gas such as nitrogen in order to prevent oxidation caused by oxygen present in the space portion in the container. For example, nitrogen bubbling of an injection solution and filling of the container in a nitrogen atmosphere can be performed.

(Release Rate)

In the liposome composition according to the present invention, the release rate of a drug (gemcitabine or a salt thereof) is preferably 10 mass %/24 hr to 70 mass %/24 hr, more preferably 20 mass %/24 hr to 60 mass %/24 hr, and still more preferably 20 mass %/24 hr to 50 mass %/24 hr.

Since the release rate depends on the temperature, it is preferable to measure release rate under a constant temperature condition. For example, in a case of humans, the temperature is not particularly limited, but it is preferable to measure the release rate within a range of body temperature (35° C. to 38° C.).

In a case where the release rate of a drug (gemcitabine or a salt thereof) is less than 15 mass %/24 hr, sufficient exposure time in the body cannot be obtained, and in many cases, the expected drug efficacy cannot be obtained. Depending on the circumstances, liposomes containing the drug remain in the body for an unnecessarily long period of time, and therefore, in some cases, unexpected toxicity may be exhibited due to accumulation of the liposomes in the tissue such as the skin in which the liposomes are hardly distributed normally. In addition, in a case where the release rate is higher than 70 mass %/24 hr, the amount of drug to be exposed per unit time increases. Therefore, the toxicity increases as the maximum blood concentration increases. In addition, the leaked drug is distributed to tissues other than a tumor site or undergoes rapid metabolism, and therefore, the retentivity in blood decreases, which is not preferable.

The method for measuring the release rate of a drug is not particularly limited. However, after administering the drug to a target mammal, model system, or the like, blood, plasma, or the like is collected from the mammal or the model system every unit time, and pretreatment or the like is performed as necessary. Moreover, the target drug can be measured through a method such as liquid high-speed chromatography or mass spectrometry.

(Method for Producing Liposome Composition)

The liposome composition according to the present invention can be produced through: an emulsification step of emulsifying a lipid dissolved in an organic solvent to form a liposome without passing through a drying and solidifying step; a drug loading step of containing gemcitabine or a salt thereof in the liposome obtained in the emulsification step; and an osmotic pressure adjusting step of adjusting the osmotic pressure of an inner aqueous phase of the liposome to 2 to 8 times the osmotic pressure of an outer aqueous phase of the liposome.

The method for producing a liposome composition may include other steps such as an evaporation step of evaporating the organic solvent used in the emulsification step, aseptic filtration, and aseptic filling as necessary.

(Emulsification Step)

In the emulsification step, an aqueous phase can be mixed with an oil phase in which at least one kind of lipid is dissolved in an organic solvent, and the aqueous solution containing the lipid can be stirred and emulsified. By performing the mixing, stirring, and emulsifying of the aqueous phase and the oil phase in which the lipid is dissolved in the organic solvent, an emulsion in which the oil phase and the aqueous phase are emulsified in an O/W type is prepared. After mixing, a part or all of the organic solvent derived from the oil phase is removed by an evaporation step to be described below to form a liposome. Alternately, a part or all of the organic solvent in the oil phase evaporates in the process of the stirring and the emulsifying to form a liposome.

As the stirring method, ultrasonic wave or mechanical shear force is used for particle miniaturization. In addition, in order to make the particle diameter uniform, an extruder treatment or a microfluidizer treatment can be performed through a filter having a constant pore diameter. Using an extruder or the like, a secondarily formed multivesicular liposome can be released to form a univesicular liposome. In the present invention, from the viewpoint of simplifying the production step, it is preferable to use a liposome in a state in which a drug is not loaded in the next step without being subjected to extrusion treatment.

In the present invention, the average particle diameter of liposomes to be prepared can be controlled by optionally selecting the speed and time of stirring. From the viewpoint of obtaining liposomes having safety and stability, it is preferable to apply shearing to an aqueous solution containing lipids at a circumferential speed of higher than or equal to 20 m/sec. The shearing is not limited. However, specifically, it is preferable to apply shearing at a circumferential speed of 20 m/sec to 35 m/sec and more preferable to apply shearing at a circumferential speed of 23 m/sec to 30 m/sec.

The emulsification step is not limited as long as it is a step of emulsification, but is preferably a step of applying high shearing and forming fine particles in an emulsification step in which an organic solvent is contained. A liposome can be formed by evaporating (removing the solvent) the organic solvent used in the emulsification step as necessary.

The liquid temperature in the emulsification step in a case of producing the liposome can be appropriately controlled. The liquid temperature at the time of mixing an oil phase with an aqueous phase is preferably higher than or equal to a phase transition temperature of a lipid to be used. For example, in a case where a lipid having a phase transition temperature of 35° C. to 40° C. is used, liquid temperature is preferably 35° C. to 70° C.

(Oil Phase)

A mixed solvent of a water-soluble organic solvent and an ester-based organic solvent is used as an organic solvent used as an oil phase. In the present invention, it is preferable not to substantially use organic solvents such as chloroform, methylene chloride, hexane, cyclohexane, and the like as organic solvents, and it is more preferable not to use these organic solvents at all.

The water-soluble organic solvent is preferably an organic solvent having a property of being optionally mixed with water. Examples of the water-soluble organic solvent include alcohols such as methanol, ethanol, n-propanol, isopropanol, n-butanol, isobutanol, and t-butanol, glycols such as glycerin, ethylene glycol, and propylene glycol, and polyalkylene glycols such as polyethylene glycol. Among these, alcohols are preferable. As alcohols, at least one selected from ethanol, methanol, 2-propanol, and t-butanol is preferable, at least one selected from ethanol, 2-propanol, and t-butanol is more preferable, and ethanol is still more preferable.

The ester-based organic solvent is preferably an ester obtained from a reaction between an organic acid and alcohol. Examples of the ester-based organic solvent include ethyl acetate, methyl acetate, isopropyl acetate, t-butyl acetate, and methyl propionate. At least one selected from ethyl acetate, isopropyl acetate, and methyl propionate is preferable, and ethyl acetate is more preferable.

The mixing ratio of the water-soluble organic solvent and the ester-based organic solvent can be set to, by mass ratio, for example, 90:10 to 30:70, and is preferably 80:20 to 40:60 and more preferably 80:20 to 70:30. The mixed solvent of the water-soluble organic solvent and the ester-based organic solvent may further contain a water-soluble solvent such as water or a buffer solution. The aqueous solvent can be added within a range of, for example, 1 to 30 mass %. The pH of the mixed solvent can be set, for example, to 3 to 10, and is preferably 4 to 9. The ester-based organic solvent may contain physiologically active substances such as various drugs soluble in these solvents.

In a case where ethanol is used as the water-soluble organic solvent and ethyl acetate is used as the ester-based organic solvent, the mixing ratio of ethanol to ethyl acetate can be set, for example, to 80:20 to 70:30 by mass ratio.

The concentration of the lipid is not particularly limited and can be appropriately adjusted. However, in a solution using a mixed solution of a water-soluble organic solvent and an ester-based organic solvent, as a solvent, the concentration can be set to 40 g/L to 250 g/L, and is preferably 100 g/L to 200 g/L.

(Aqueous Phase)

The aqueous phase means an outer aqueous phase and an inner aqueous phase.

The outer aqueous phase in the present invention means an aqueous solution in which liposomes are dispersed. In a case of injections, for example, a solution occupying the outside of liposomes of a liposome dispersion liquid stored by being packaged in a vial or a prefilled syringe becomes an outer aqueous phase. In addition, regarding a solution dispersed at the time of use during administration using an attached liquid for dispersion or other dissolution liquid, a solution occupying the outside of liposomes of a liposome dispersion liquid becomes an outer aqueous phase.

The inner aqueous phase in the present invention means an aqueous phase in a closed endoplasmic reticulum separated by a lipid bilayer membrane of a liposome.

In a case of producing liposomes, water (distilled water, water for injection, or the like), physiological saline, various buffer solutions or aqueous solutions of saccharides, and a mixture thereof (aqueous solvent) are preferably used as aqueous solutions (outer aqueous phases) in which liposomes are dispersed. The buffer solution is not limited to an organic type and an inorganic type. However, a buffer solution having a buffering action in the vicinity of the hydrogen ion concentration close to a body fluid is suitably used, and examples thereof include a phosphate buffer solution, a Tris buffer solution, a citrate buffer solution, an acetate buffer solution, and Good's buffer solution. The pH of an aqueous phase can be set, for example, to 5 to 9, and is preferably 7 to 8. It is preferable to use a phosphate buffer solution (for example, pH=7.4) as the aqueous solution (outer aqueous phase) in which liposomes are dispersed. In a case of producing liposomes, an inner aqueous phase of liposomes may be an aqueous solution in which liposomes are dispersed, or water, physiological saline, various buffer solutions or aqueous solutions of saccharides, and a mixture thereof. Water used as an outer aqueous phase or an inner aqueous phase preferably does not contain impurities (such as dust and chemical substances).

The physiological saline means an inorganic salt solution adjusted so as to be isotonic with a human body, and may have a buffering function. Examples of the physiological saline include saline containing 0.9 w/v % sodium chloride, phosphate-buffered physiological saline (hereinafter, also referred to as PBS), and Tris-buffered physiological saline.

An aqueous solution containing liposomes prepared through the emulsification step is subjected to after-treatment through methods such as centrifugal separation, ultrafiltration, dialysis, gel filtration, or freeze-drying in order to remove components not contained in the liposomes or adjust the concentration or osmotic pressure.

(Extrusion Treatment)

Extrusion treatment means a step of applying a physical shear force by passing liposomes through a filter having pores for atomization. In the case of passing the liposomes through the filter, the atomization can be rapidly performed by keeping the temperature of a liposome dispersion liquid and the filter at a temperature higher than or equal to the phase transition temperature of membranes forming the liposomes.

(Evaporation Step)

An evaporation step may be provided in the method for producing a liposome composition as necessary. In the evaporation step, an organic solvent is evaporated from an aqueous solution containing the liposomes obtained in the emulsification step. In the present invention, the evaporation step includes at least a step of forcibly removing a part or all of the organic solvent derived from an oil phase as an evaporation step and a step of naturally evaporating a part or all of the organic solvent in an oil phase in the process of stirring and emulsifying.

The method for evaporating an organic solvent in the evaporation step is not particularly limited. However, for example, at least one of a step of evaporating an organic solvent through heating, a step of being left to stand or continuing gentle stirring after the emulsification, and a step of performing vacuum degassing may be performed.

In the step of evaporating an organic solvent, it is preferable to set the concentration of the organic solvent contained in an aqueous solution containing liposomes to less than or equal to 15 mass % within 30 minutes from the start of the step of evaporating an organic solvent.

(Drug Loading Step)

In the drug loading step, in a case where a drug (gemcitabine or a salt thereof) is contained in a liposome, the drug can be dissolved in an aqueous medium in which the drug is hydrated and swollen, and can be contained in an inner aqueous phase of the liposome through a method such as heating at a temperature higher than or equal to the phase transition temperature, ultrasonic treatment, or extrusion. In addition, the drug can be dissolved in the aqueous phase during lipid emulsification and be contained in the inner aqueous phase.

(Osmotic Pressure Adjusting Step)

The osmotic pressure adjusting step means a step of adjusting the osmotic pressure of an inner aqueous phase and an outer aqueous phase of a liposome. The release rate can be controlled by adjusting the osmotic pressure of an inner and an outer aqueous phase of a liposome. The osmotic pressure adjusting step is not particularly limited, but an example thereof includes dialysis. In the production method of the present invention, it is preferable to simultaneously perform a step of containing a nucleic acid analog anticancer agent in a liposome and the osmotic pressure adjusting step from the viewpoint of production efficiency.

Solutes of an outer aqueous phase and an inner aqueous phase in liquid obtained after the drug loading step are homogenized, and the osmotic pressure at that time can be defined as an osmotic pressure of the inner aqueous phase of the liposome to be obtained. However, in the subsequent step of adjusting osmotic pressure and substituting performed through dialysis of an outer aqueous phase, a heating operation is limited to a case where a solute of an inner aqueous phase is sufficiently held, for example, by controlling the temperature to be lower than or equal to the phase transition temperature a lipid. The osmotic pressure of an outer aqueous phase can also be defined as an osmotic pressure of a dialysis solution used in the final dialysis step. However, this is limited to a case where it is possible to sufficiently perform replacement with the dialysis solution. In addition, regarding the obtained liquid of a liposome composition, it is also possible to obtain the osmotic pressures of an inner aqueous phase and an outer aqueous phase by quantitatively determining the composition concentration of a solute of the outer aqueous phase and the composition concentration of a solute of the inner aqueous phase through centrifugal separation or ultrafiltration, and measuring the osmotic pressure of the composition liquid.

The osmotic pressure of the inner aqueous phase of the liposome is preferably adjusted to 2 to 8 times the osmotic pressure of the outer aqueous phase of the liposome, more preferably 2.5 to 6 times the osmotic pressure of the outer aqueous phase of the liposome, and still more preferably 3 to 5 times the osmotic pressure of the outer aqueous phase of the liposome.

The osmotic pressure may be measured according to an osmometry method disclosed in the Japanese Pharmacopoeia, 16th Edition. More specifically, the osmolality can be obtained by measuring the freezing point descending degree of water. In addition, the freezing point descending degree of water is defined by the solute molarity, and the osmolality can also be obtained from the solute molarity.

The osmotic pressure of the outer aqueous phase exerts an essential effect on the living body during administration. In a case where the osmotic pressure of the outer aqueous phase is far from osmotic pressure of body fluid, hemolysis or pain is caused due to movement of water in each tissue. Accordingly, the osmotic pressure of the outer aqueous phase is preferably 200 mOsmol/L to 400 mOsmol/L, more preferably 250 mOsmol/L to 350 mOsmol/L, and still more preferably isotonic with the body fluid.

Aseptic Filtration

The liposome composition is preferably subjected to aseptic filtration. As a filtration method, unnecessary substances can be removed from an aqueous solution containing liposomes using a hollow fiber membrane, a reverse osmosis membrane, a membrane filter, or the like. In the present invention, the filtration is preferably performed using a filter having a sterilizable pore diameter (preferably a 0.2 μm filtration sterilization filter).

In order to prevent the influence on the average particle diameter due to deformation of liposomes, it is preferable to carry out the aseptic filtration step and the aseptic filling step, to be described below, at a temperature lower than or equal to the phase transition temperature of a lipid forming the liposome. For example, in a case where the phase transition temperature of the lipid is around 50° C., about 0° C. to 40° C. is preferable and about 5° C. to 30° C. is more specifically preferable.

(Aseptic filling)

The liposome composition obtained after the aseptic filtration is preferably subjected to aseptic filling for medical use. A well-known aseptic filling method can be applied. It is possible to prepare a suitable liposome composition for medical use by aseptically filling a container therewith.

(Tumor Therapeutic Agent)

The tumor therapeutic agent of the present invention may contain additives such as an excipient, a binder, a lubricant, a disintegrator, a coloring agent, a flavoring agent, an emulsifying agent, a surfactant, a solubilizing agent, a suspending agent, an isotonic agent, a buffer agent, a preservative, an antioxidant, a stabilizer, and an absorption promoter which have been used for formulation.

The tumor therapeutic agent of the present invention may be a 1-pack type formulation containing a taxane antitumor agent and a liposome composition in which gemcitabine or a salt thereof is contained in a liposome, or a 2-pack type formulation with a taxane antitumor agent and a liposome composition in which gemcitabine or a salt thereof is contained in a liposome. The tumor therapeutic agent is preferably a 2-pack type formulation having a taxane antitumor agent and a liposome composition in which gemcitabine or a salt thereof is contained in a liposome, as separate formulations.

In the case of using a tumor therapeutic agent including a taxane antitumor agent and a liposome composition in which gemcitabine or a salt thereof is contained in a liposome, as separate formulations, it is possible to administer each formulation to a target simultaneously, separately, continuously, or at intervals.

Examples of administration routes of the tumor therapeutic agent of the present invention include an intravenous injection method, an intraarterial injection method, an intrarectal injection method, an intraperitoneal injection method, an intramuscular injection method, an intratumoral injection method, or an intravesical injection method, or methods such as oral administration, transdermal administration, and a method using suppositories.

Parenteral administration is preferable as an administration route of the liposome composition. Examples thereof include intravenous injection such as instillation, intramuscular injection, intraperitoneal injection, subcutaneous injection, intraocular injection, and intrathecal injection. An example of the administration method includes administration using a syringe or through instillation.

Oral administration is preferable as an administration route of a taxane antitumor agent.

In the tumor therapeutic agent of the present invention, for example, a liposome composition in which gemcitabine or a salt thereof is contained in a liposome can be parenterally administered, and a taxane antitumor agent can be orally administered.

Regarding the dosage and the number of times of administration of gemcitabine or a salt thereof contained in a liposome composition, 1 to 4 mg/kg of gemcitabine or a salt thereof can be administered once or several times dividedly per day. For example, it is preferable to administer 60 mg to 240 mg of an injection, preferably 120 mg to 240 mg of an injection, and more preferably 180 mg to 240 mg of an injection per day through intravenous injection for human (patient; with a body weight of 60 kg). However, the dosage and the number of times of administration is not limited.

Regarding the dosage and the number of times of administration of taxane antitumor agent, 0.01 mg/kg to 1000 mg/kg of the taxane antitumor agent can be administered once or several times dividedly per day.

Examples of dosage forms of the tumor therapeutic agent of the present invention include tablets, capsules, suspensions, emulsions, solutions, eye drops, nasal drops, ear drops, and injections.

Tumors for which the tumor therapeutic agent of the present invention can be effectively used are not particularly limited as long as they are carcinomas and sarcomas, but examples thereof include breast cancer, endometrial cancer, ovarian cancer, prostate cancer, lung cancer, stomach cancer (gastric adenocarcinoma), non-small-cell lung cancer, pancreatic cancer, and head and neck squamous cell cancer, and pancreatic cancer is preferable.

(Kit)

The kit of the present invention is a kit including a combination of (a) liposome composition in which gemcitabine or a salt thereof is contained and (b) taxane antitumor agent.

In the kit of the present invention, (a) liposome composition in which gemcitabine or a salt thereof is contained and (b) taxane antitumor agent can each be in various well-known formulation forms, and are stored in various containers which are normally used depending on the formulation forms.

In the kit of the present invention, (a) liposome composition in which gemcitabine or a salt thereof is contained and (b) taxane antitumor agent may be stored in separate containers respectively, or may be mixed with each other and stored in the same container. It is preferable that (a) liposome composition in which gemcitabine or a salt thereof is contained and (b) taxane antitumor agent are stored in separate containers respectively.

(Antitumor Effect Enhancing Agent)

The antitumor effect enhancing agent of the present invention may contain additives such as an excipient, a binder, a lubricant, a disintegrator, a coloring agent, a flavoring agent, an emulsifying agent, a surfactant, a solubilizing agent, a suspending agent, an isotonic agent, a buffer agent, a preservative, an antioxidant, a stabilizer, and an absorption promoter which have been used for formulation.

It is possible to administer the antitumor effect enhancing agent of the present invention and the taxane antitumor agent to a target simultaneously, separately, continuously or at intervals.

Parenteral administration is preferable as an administration route of the antitumor effect enhancing agent of the present invention. Examples thereof include intravenous injection such as instillation, intramuscular injection, intraperitoneal injection, subcutaneous injection, intraocular injection, and intrathecal injection. An example of the administration method includes administration using a syringe or through instillation.

Regarding the dosage and the number of times of administration of gemcitabine or a salt thereof contained in the antitumor effect enhancing agent of the present invention, 1 mg/kg to 4 mg/kg of gemcitabine or a salt thereof can be administered once or several times dividedly per day. For example, it is preferable to administer 60 to 240 mg of an injection, preferably 120 mg to 240 mg of an injection, and more preferably 180 mg to 240 mg of an injection per day through intravenous injection for human (patient; with a body weight of 60 kg). However, the dosage and the number of times of administration of the antitumor effect enhancing agent of the present invention are not limited.

Tumors for which the antitumor effect enhancing agent of the present invention can be effectively used are not particularly limited as long as they are carcinomas and sarcomas in which a taxane antitumor agent is used. However, examples thereof include breast cancer, endometrial cancer, ovarian cancer, prostate cancer, lung cancer, stomach cancer (gastric adenocarcinoma), non-small-cell lung cancer, pancreatic cancer, head and neck squamous cell cancer, esophageal cancer, bladder cancer, melanoma, colorectal cancer, renal cell carcinoma, non-Hodgkin lymphoma, and urothelial cancer, and pancreatic cancer is preferable.

EXAMPLES

Hereinafter, the present invention will be described in detail using examples. However, the present invention is not limited to the examples.

Regarding the average particle diameter, a sample was diluted to 1,000 times by mass using 1×PBS (manufactured by NIPPON GENE CO., LTD.) and the volume average particle diameter was measured through a dynamic light scattering method using a NANOTRAC UPA-UT (manufactured by Nikkiso Co., Ltd.)

The volume of a tumor was calculated using the following equation by measuring the major axis (a) and the minor axis (b) of the tumor with calipers.

Equation: $(a \times b^2) \times 0.5$ (where "a" is the major axis and "b" is the minor axis)

Reference Example 1 a) Preparation of Oil Phase 16.6 g, 2.0 g, and 4.3 g of hydrogenated soybean phosphatidylcholine, cholesterol, and an N-(carbonyl-methoxypolyethylene glycol 2000)-1,2-distearoyl-sn-glycero-3-phosphoethanolamine sodium salt (hereinafter, also referred to as DSPE-PEG) were respectively taken so as to have a molar ratio of 76/19/5. Subsequently, 405 ml of an organic solvent (ethanol/ethyl acetate=3/1) was added thereto and lipids are dissolved at a heated temperature of 70° C. to obtain an oil phase.

b) Preparation of Aqueous Phase

A 4 mM phosphate buffer solution (pH of 7.78) was prepared and used as an aqueous phase.

c) Preparation of Drug Non-Contained Liposome

The aqueous phase was heated to 70° C. and the oil phase was added thereto so that the volume ratio of water phase/oil phase=8/3, and then, the aqueous phase and the oil phase were mixed using a rotary stirring emulsifier at a circumferential speed of 20 m/s at 13,000 rpm for 30 minutes. Thereafter, the organic solvent and water were evaporated by supplying nitrogen while heating the mixture to higher than or equal to a phase transition temperature, and the mixture was concentrated so as to became a volume of about ¹⁄₁₀ of the volume before emulsification, to obtain a drug non-contained liposome. The average particle diameter at this time was 68.0 nm.

d) Batch Mixing of Drug Non-Contained Liposomes

Two batches of drug non-contained liposomes prepared in c) were mixed with each other.

e) Preparation of Drug Contained Liposome

Gemcitabine hydrochloride was used as a drug. Gemcitabine hydrochloride was purchased from TEVA. 81.63 g of sodium chloride, 29.01 g of disodium hydrogen phosphate dodecahydrate, and 2.29 g of sodium dihydrogen phosphate dihydrate were dissolved in 948 g of water for injection to prepare PBS. 12.98 g of gemcitabine hydrochloride, 54.01 g of PBS, 75.74 g of water for injection of Japanese Pharmacopoeia, and 2.71 mL of 8 M sodium hydroxide were mixed with each other in two containers to prepare drug solutions. 141.4 mL of a drug non-contained liposome and 2.71 mL of 8 M sodium hydroxide were added to and mixed with each of the drug solutions. The osmotic pressures of the solutions are 1,039 mOsm/L, which are osmotic pressures of inner aqueous phases of obtained liposome compositions. Next, solutions were heated at 70° C. for 10 minutes, and then, cooled to 40° C. and diluted with a 1,016 mM sucrose/37 mM histidine solution. After the dilution, the solutions were combined into one solution to prepare a drug loading solution. A 275 mM sucrose/10 mM histidine aqueous solution was prepared as a obtained dialysis solution of the liposome composition through dialysis. The osmotic pressure obtained from the solute molarity of this solution was 285 mOsm/L. Dialysis was performed at room temperature using this dialysis solution, each solute and non-contained gemcitabine hydrochloride present in the outer aqueous phase of the drug loading solution were removed, and the outer aqueous phase was replaced with the dialysis solution. A gemcitabine-contained liposome composition having a gemcitabine hydrochloride concentration of 0.81 mg/mL, an average particle diameter of 74.9 nm, an inner aqueous phase osmotic pressure of 1,039 mOsm/L, an outer aqueous phase osmotic pressure of 285 mOsm/L, and an osmotic pressure of an inner aqueous phase with respect to an outer aqueous phase of 3.6 times was obtained through the above-described step. The content ratio of cholesterols with respect to the total amount of lipids forming a liposome was 19.3 mol %.

The osmotic pressure was calculated from the solute molarity.

Reference Example 2

Measurement of Release Rate in Plasma

50 μL of a liposome composition was diluted (volume) 20 times with mouse plasma and incubated at 37° C. for 24 hours, and 100 μL was collected at a point in time of 24 hours. Subsequently, centrifugal filtration was carried out using an ultrafiltration filter (AMICON ULTRA-0.5 with 10 kDa manufactured by Millipore) under the conditions of 7,400×g, for 30 minutes, and at 4° C. The amount of drug contained in the collected filtrate was quantitatively determined by HPLC and the release rate was calculated by the following equation.

Equation: Release rate (%/24 hr)=(amount of drug in filtrate after 24 hours of incubation)×20÷amount of drug contained in all phases of liposome composition×100

The result was 24%/24 hr.

Example 1

Pharmacological test on Capan-1 subcutaneous transplantation tumor-bearing mouse model Gemcitabine (hereinafter, also referred to as Gem), abraxane (hereinafter, also referred to as Abx), and a gemcitabine-contained liposome composition (hereinafter, also referred to as a composition A) were used as test substances.

Gem was prepared by dissolving gemcitabine hydrochloride (manufactured by TEVA) in physiological saline. Abx obtained by dissolving abraxane (manufactured by Celgene) in physiological saline was used. A gemcitabine-contained liposome composition prepared in Reference Example 1 was used.

$1 \times 10^7$ Capan-1 cells of a human pancreatic cancer cell strain were transplanted subcutaneously into the flank of a female nude mouse to form subcutaneous tumors. The effect of controlling the subcutaneous tumor in combination administration of Abx and the composition A was evaluated using the volume of the tumor as an index. As test substances, a sucrose solution was used as a group 1, Gem was used as a group 2, a composition A was used as a group 3, Abx and Gem were respectively used as a group 4 and a group 5, and Abx and a composition A were respectively used as a group 6 and a group 7. Groups 1 to 5 are comparative examples and groups 6 and 7 are examples. All test substances were administered to the tail vein once a week from day 17 after transplantation for a total of 3 weeks.

Regarding the dosage of each drug, the amount at which the weight loss rate does not exceed 20% was set as a dose which may not reach a severe minimum weight so that the recovery of a maximum tolerable dose (MTD) is not recognized.

The compositions of the groups and the dosages are shown in Table 1.

TABLE 1

| Group | Test substance | Dosage (amount as paclitaxel or gemcitabine which is activator) (mg/kg/times) | | Administration route | Administration schedule | Administration dose (mL/kg) |
|---|---|---|---|---|---|---|
| | | Paclitaxel | Gemcitabine | | | |
| 1 | 9.4% sucrose solution | 0 | 0 | Tail vein | Once a week for 3 weeks | 10 |
| 2 | Gem | 0 | 240 | Tail vein | Once a week for 3 weeks | 10 |
| 3 | Composition A | 0 | 3 | Tail vein | Once a week for 3 weeks | 10 |
| 4 | Abx + Gem | 30 | 240 | Tail vein | Once a week for 3 weeks | 10 |
| 5 | Abx + Gem | 100 | 240 | Tail vein | Once a week for 3 weeks | 10 |
| 6 | Abx + composition A | 30 | 3 | Tail vein | Once a week for 3 weeks | 10 |
| 7 | Abx + composition A | 100 | 3 | Tail vein | Once a week for 3 weeks | 10 |

Figure 1:
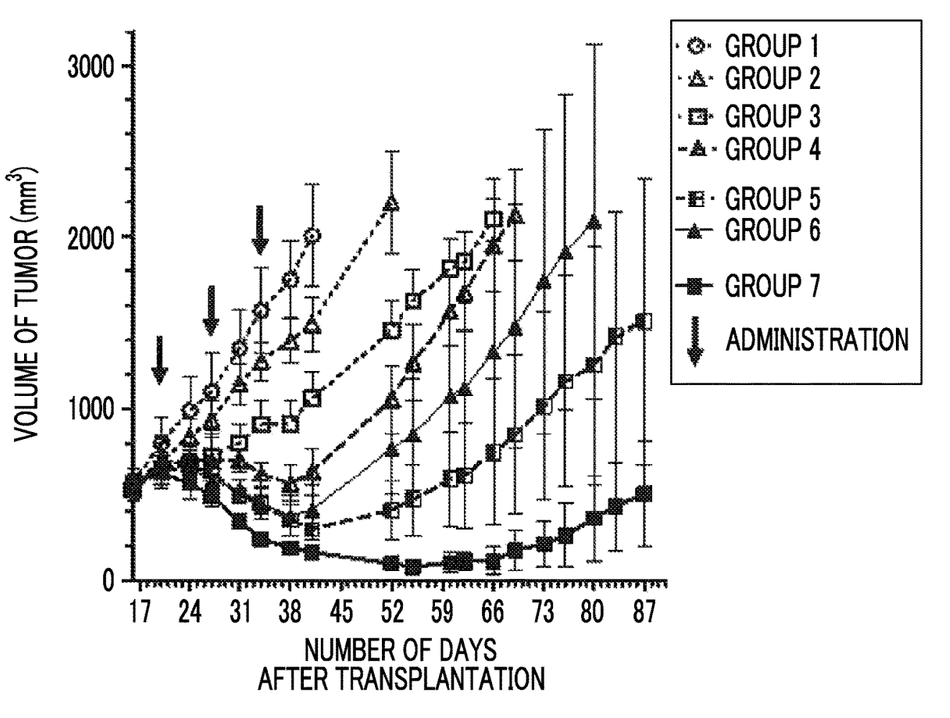
FIG. 1 is a graph showing transition of a volume of a tumor in a Capan-1 subcutaneous transplantation tumor-bearing mouse model.

The transition of the volume of a tumor is shown in FIG. 1.

Table 2 shows the tumor volume average value on day 38 after transplantation, the tumor volume standard deviation on day 38 after transplantation, the tumor regression rate from the start of medication, and the number of days until the tumor volume average value of 2,000 mm$^3$ is reached.

Tukey's multiple comparisons test was performed as a statistical analysis, and a P value less than 5% among the groups was determined to indicate that there is a statistically significant difference. Graphpad Prism version 5.03 was used for data processing.

In Table 2, a indicates P<0.001 by comparison with the group 1, b indicates P<0.001 by comparison with the group 2, c indicates P<0.05 by comparison with the group 4, and N.R. indicates no regression.

TABLE 2

| Group | Tumor volume average value (mm$^3$) on day 38 after transplantation | Tumor volume standard deviation on day 38 after transplantation | Tumor regression rate (%) from start of medication | Number of days until tumor volume average value of 2,000 mm$^3$ is reached |
|---|---|---|---|---|
| 1 | 1747 | 229 | N.R. | 41 |
| 2 | 1397$^{a)}$ | 125 | N.R. | 52 |
| 3 | 917$^{a),b)}$ | 136 | N.R. | 66 |
| 4 | 565$^{a)}$ | 105 | N.R. | 69 |
| 5 | 375$^{a)}$ | 120 | 31 | 80 |
| 6 | 349$^{a),c)}$ | 89 | 47 | >87 |
| 7 | 190$^{a)}$ | 33 | 86 | >87 |

$^{a)}$P < 0.001 by comparison with group 1,
$^{b)}$P < 0.001 by comparison with group 2,
$^{c)}$P < 0.05 by comparison with group 4
N.R.: no regression The volume of a tumor on day 38 after transplantation in the group 6 or 7 is smaller than that in the group 4 or 5, and the group 6 shows a statistically significant difference (P<0.05) compared to the group 4. In addition, regarding the tumor regression rate from the start of medication, there was no tumor regression in the group 4. The tumor regression rate in the group 6 was 47% and tumor regression rate in the group 7 was 86%, whereas the tumor regression rate in the group 5 was 31%. The groups 6 and 7 showed an excellent tumor regression effect. In addition, the number of days until the tumor volume average of 2,000 mm$^3$ was reached in each of the groups 6 and 7 was >87, whereas the number of days until the tumor volume average of 2,000 mm$^3$ was reached in each of the groups 4 and 5 was 69 days after transplantation and 80 days after transplantation.

It is shown from the above-described results that the composition A has an effect of suppressing the growth of Capan-1 tumor cells transplanted subcutaneously into the nude mice in combination with Abx, and its growth suppressing effect is higher than that of the combined use of Gem and Abx.

What is claimed is:

1. A tumor therapeutic agent obtained by combining a taxane antitumor agent with a liposome composition in which gemcitabine or a salt thereof is contained in a liposome,
    wherein the taxane antitumor agent is nab-paclitaxel,
    the liposome comprises a lipid, and the lipid comprises hydrogenated soybean phosphatidylcholine, 1,2-distearoyl-3-phosphatidylethanolamine-polyethylene glycol, and cholesterol,
    the content ratio of cholesterols to the total amount of lipid forming the liposome is 10 mol % to 25 mol %,
    the osmotic pressure of an inner aqueous phase of the liposome is 2 to 8 times the osmotic pressure of an outer aqueous phase of the liposome,
    the tumor therapeutic agent is a 2-pack formulation having a taxane antitumor agent and a liposome composition in which gemcitabine or a salt thereof is contained in a liposome, as separate formulations, and
    the taxane antitumor agent and the liposome composition are in synergistic effect and effective amounts.

2. The tumor therapeutic agent according to claim 1, wherein the liposome is a single lamella.

3. The tumor therapeutic agent according to claim 1, wherein a release rate of the gemcitabine or the salt thereof from the liposome composition in plasma is 10 mass %/24 hr to 70 mass %/24 hr.

4. The tumor therapeutic agent according to claim 1, wherein an average particle diameter of the liposome is 2 nm to 200 nm.

* * * * *